US010270995B1

United States Patent
Clajus et al.

(10) Patent No.: US 10,270,995 B1
(45) Date of Patent: Apr. 23, 2019

(54) AUTOMATED NON-CONFORMING PIXEL MASKING

(71) Applicant: KROMEK GROUP, PLC

(72) Inventors: Rolf Martin Clajus, Los Angeles, CA (US); Franklin Dean Walker, San Dimas, CA (US); James William Hugg, Mars, PA (US); Brian William Harris, Gibsonia, PA (US)

(73) Assignee: KROMEK GROUP, PLC, Sedgefield, County Durham (GB)

( * ) Notice: Subject to any disclaimer, the term of this patent is extended or adjusted under 35 U.S.C. 154(b) by 0 days.

(21) Appl. No.: 15/788,147

(22) Filed: Oct. 19, 2017

(51) Int. Cl.
*H04N 5/367* (2011.01)
*G06T 11/00* (2006.01)
*G06T 5/00* (2006.01)

(52) U.S. Cl.
CPC ........... *H04N 5/3675* (2013.01); *G06T 5/004* (2013.01); *G06T 11/005* (2013.01)

(58) Field of Classification Search
CPC ...... H04N 5/367; H04N 5/3675; H04N 5/365; H04N 5/2176; H04N 5/3651; H04N 5/3456; H04N 5/345; G06T 5/004; G06T 11/005; G06T 2207/10072; G06T 7/0012
See application file for complete search history.

(56) References Cited

U.S. PATENT DOCUMENTS

| | | | | |
|---|---|---|---|---|
| 6,381,374 B1* | 4/2002 | Pourjavid | .............. | H04N 5/367 348/E5.081 |
| 6,529,622 B1* | 3/2003 | Pourjavid | .............. | H04N 5/367 250/370.09 |
| 7,009,644 B1* | 3/2006 | Sanchez | ............... | H04N 5/2173 348/243 |
| 7,427,759 B1* | 9/2008 | Pruvot | ................... | G06K 19/18 250/338.1 |
| 2004/0095488 A1* | 5/2004 | Rambaldi | .............. | H04N 5/367 348/246 |
| 2007/0165934 A1* | 7/2007 | Maac | ...................... | G06T 5/005 382/132 |
| 2011/0080505 A1* | 4/2011 | Ogino | .................... | H04N 5/365 348/246 |
| 2011/0235940 A1* | 9/2011 | Pavkovich | .............. | G06T 5/005 382/275 |
| 2012/0113299 A1* | 5/2012 | Palik | ........................ | G06T 5/50 348/241 |
| 2015/0170376 A1* | 6/2015 | Bishop | ................... | G06T 5/005 382/167 |

* cited by examiner

*Primary Examiner* — Carol Wang
(74) *Attorney, Agent, or Firm* — Ference & Associates LLC

(57) ABSTRACT

One embodiment provides a method, including: receiving a plurality of communication events associated with a pixel of an imaging device; identifying a frequency associated with the communication events, wherein the identifying a frequency comprises determining a number of communication events occurring within a predetermined time interval or determining a time interval between the communication events; determining, from the identified frequency, whether the pixel comprises a non-conforming pixel; and masking, if the pixel comprises a non-conforming pixel, subsequent communication events from the non-conforming pixel. Other aspects are described and claimed.

17 Claims, 6 Drawing Sheets

AUTOMATED NON-CONFORMING PIXEL MASKING

BACKGROUND

Imaging devices perform many different functions such as medical imaging, security screening, image capture, or the like. The source of the imaging may be a radiological source, visible light, non-visible light, or any type of source for which the imaging device is capable of detection. For example, in a medical setting, a patient may be injected with a radiological agent and the imaging device may capture the emission of radiation from the patient's body for diagnostic analysis. As another example, in a security screening scenario, an individual's body or personal effect may be placed in an imaging device or scanner to search for prohibited materials. The imaging device may include a camera sensitive to the emission source, for example, a camera including a specific substance or object that is sensitive to or reacts to the emission source. The camera may contain individual pixels which may allow the image to determine both the location and intensity of the emitted signal.

BRIEF SUMMARY

In summary, one aspect provides a method, comprising: receiving a plurality of communication events associated with a pixel of an imaging device; identifying a frequency associated with the communication events, wherein the identifying a frequency comprises determining a number of communication events occurring within a predetermined time interval or determining a time interval between the communication events; determining, from the identified frequency, whether the pixel comprises a non-conforming pixel; and masking, if the pixel comprises a non-conforming pixel, subsequent communication events from the non-conforming pixel.

Another aspect provides an information handling device, comprising: a processor; a memory device that stores instructions executable by the processor to: receive a plurality of communication events associated with a pixel of an imaging device; identify a frequency associated with the communication events, wherein the identifying a frequency comprises determining a number of communication events occurring within a predetermined time interval or determining a time interval between the communication events; determine, from the identified frequency, whether the pixel comprises a non-conforming pixel; and mask, if the pixel comprises a non-conforming pixel, subsequent communication events from the non-conforming pixel.

A further aspect provides a product, comprising: a storage device that stores code, the code being executable by a processor and comprising: code that receives a plurality of communication events associated with a pixel of an imaging device; code that identifies a frequency associated with the communication events, wherein the identifying a frequency comprises determining a number of communication events occurring within a predetermined time interval or determining a time interval between the communication events; code that determines, from the identified frequency, whether the pixel comprises a non-conforming pixel; and code that masks, if the pixel comprises a non-conforming pixel, subsequent communication events from the non-conforming pixel.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
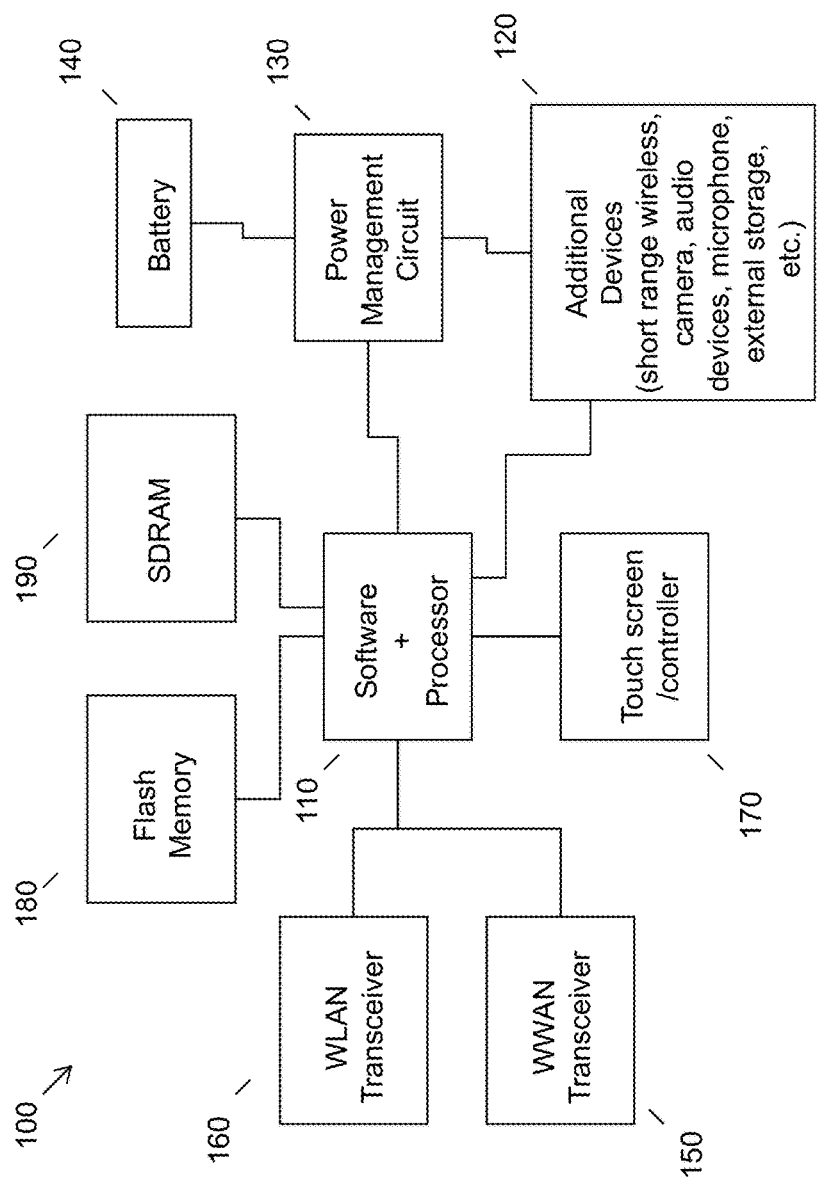
FIG. 1 illustrates an example of information handling device circuitry.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Users of imaging devices often desire image output of a high spatial and energy resolution. For example, in a medical image with high spatial and energy resolution may influence a patient's care by directing a physician to a location of interest within the patient's body. Many imaging devices utilize a camera sensitive to the type of emission being imaged in order to accurately capture an image. In order to capture the image, the camera image is divided into discrete areas or pixels, where each pixel may represent both a location and an intensity within the image captured.

As with any device, there exists the possibility of a malfunction or non-conforming-pixel (picture element). A non-conforming pixel or plurality of pixels improperly represents a true image of the source. An example of this is a consumer digital camera that captures an image and the image contains a "dead" or non-working pixel. A "dead" pixel may be represented within the photographer's image as a pixel or spot within the image that is black, grey, a color not represented by the original field of view, or the like. This is because a dead pixel provides no signal to the image processor so that the image processor can accurately represent the portion of the image covered by the pixel. In a medical or security setting, these non-conforming, dead, or overactive pixels represent a loss of time, resources, security, and/or patient care with favorable outcomes, because the pixels are not providing accurate representations of what is actually being imaged. In this disclosure a non-conforming pixel may refer to a pixel that is dead, unresponsive, overactive, hot, or fails to conform to performance parameters required by the imaging system.

Currently, in order to prevent communications from a non-conforming pixel, a human operator must identify the non-conforming pixel and program the device to prevent communications from being received from the non-conforming pixel. For example, a service technician may be called to the location of the imaging device in order to diagnose the location of the non-conforming pixel and program the device to ignore communications from the non-conforming pixel. A non-conforming pixel that is overactive or "hot" provides too many communications within a short period of time. All these communications can result in inaccurate imaging, for example, due to a plurality of overactive pixels the image may appear to have many locations within the patient that are of concern. Alternatively, an overactive pixel may dominate the communications from a local region of the imaging device, thus effectively suppressing other local pixels from communicating properly. Calling a technician to fix a non-conforming pixel not only takes time and costs money, but may also prevent the imaging device from being used for imaging which may result in cancelled appointments, inaccurate images that must be retaken, or the like.

Accordingly, an embodiment provides a system and method of automatically identifying non-conforming pixels and masking subsequent communication events from the at least one non-conforming pixel in an imaging device. The imaging system may receive a plurality of communication events associated with a pixel of an imaging device, and each communication event may correspond to an interaction between a particle or photon with a pixel of an imaging device. A communication event may also be called a trigger event or simply a trigger. One technique for determining if a pixel is a non-conforming pixel, is provided by an embodiment identifying a frequency associated with the communication events. An embodiment may identify a frequency by determining a number of communication events occurring within a predetermined time interval and determining a time interval between the communication events occurring within the predetermined time interval. In an embodiment, the system and method may determine, from the identified frequency, whether the pixel comprises a non-conforming pixel. In an embodiment, if the pixel comprises a non-conforming pixel then subsequent communication events from the non-conforming pixel may be masked.

The illustrated example embodiments will be best understood by reference to the figures. The following description is intended only by way of example, and simply illustrates certain example embodiments.

One embodiment of automated non-conforming pixel masking applies to smart phones, tablets, and the like, that ubiquitously include a pixelated optical photography camera and display of the pixelated image. While various other circuits, circuitry or components may be utilized in information handling devices, with regard to smart phone and/or tablet circuitry 100, an example illustrated in FIG. 1 includes a system on a chip design found for example in tablet or other mobile computing platforms. Software and processor(s) are combined in a single chip 110. Processors comprise internal arithmetic units, registers, cache memory, busses, I/O ports, etc., as is well known in the art. Internal busses and the like depend on different vendors, but essentially all the peripheral devices (120) may attach to a single chip 110. The circuitry 100 combines the processor, memory control, and I/O controller hub all into a single chip 110. Also, systems 100 of this type do not typically use SATA or PCI or LPC. Common interfaces, for example, include SDIO and I2C.

There are power management chip(s) 130, e.g., a battery management unit, BMU, which manage power as supplied, for example, via a rechargeable battery 140, which may be recharged by a connection to a power source (not shown). In at least one design, a single chip, such as 110, is used to supply BIOS like functionality and DRAM memory.

System 100 typically includes one or more of a WWAN transceiver 150 and a WLAN transceiver 160 for connecting to various networks, such as telecommunications networks and wireless Internet devices, e.g., access points. Additionally, devices 120 are commonly included, e.g., an image sensor such as a camera. System 100 often includes a touch screen 170 for data input and display/rendering. System 100 also typically includes various memory devices, for example flash memory 180 and SDRAM 190. The components described herein may be adapted for use in an imaging device.

Figure 2:
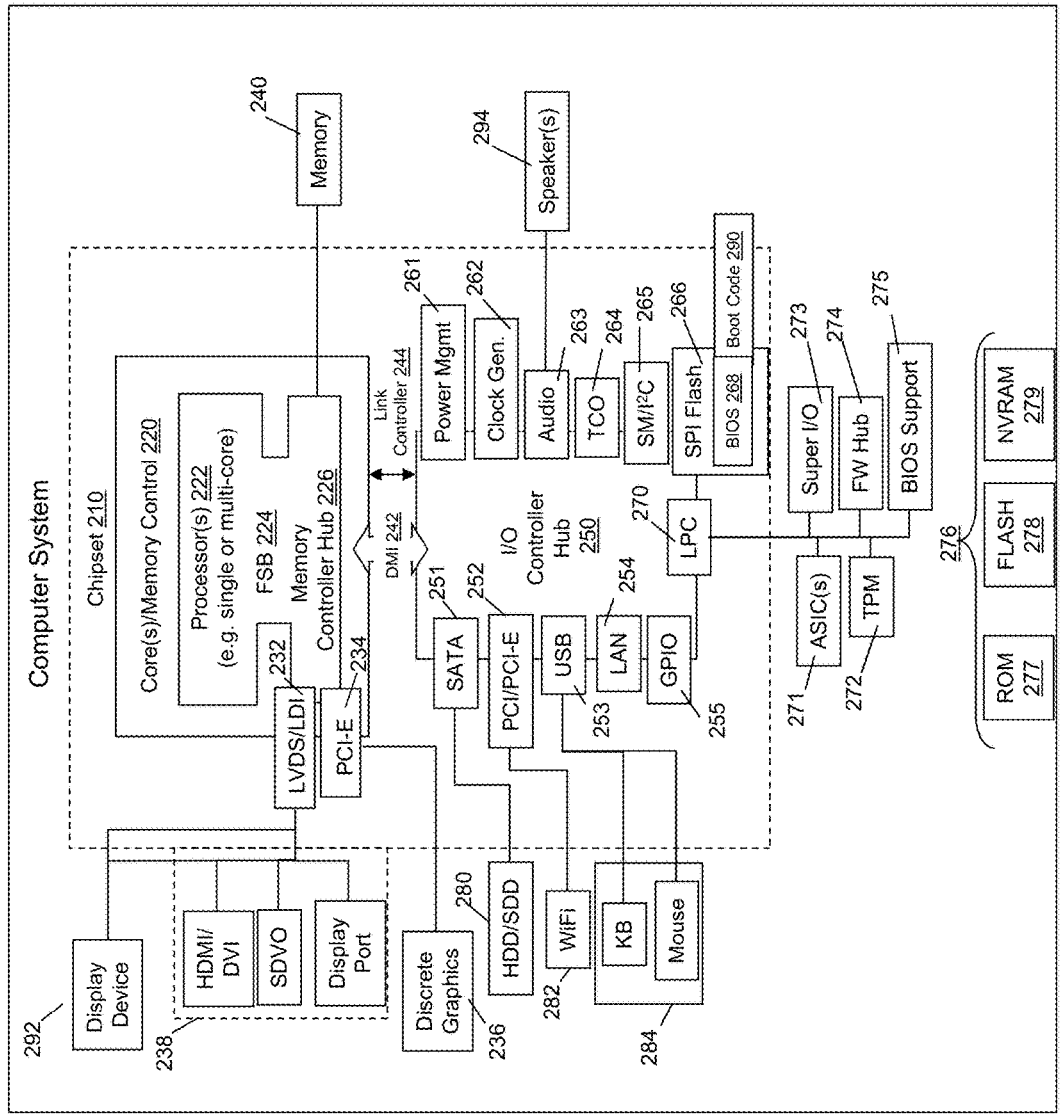
FIG. 2 illustrates another example of information handling device circuitry.

FIG. 2 depicts a block diagram of another example of information handling device circuits, circuitry or components. The example depicted in FIG. 2 may correspond to computing systems such as personal computers, laptop computers, or other devices that may embody automated non-conforming pixel masking for the pixelated digital cameras such devices ubiquitously comprise. As is apparent from the description herein, embodiments may include other features or only some of the features of the example illustrated in FIG. 2.

The example of FIG. 2 includes a so-called chipset 210 (a group of integrated circuits, or chips, that work together, chipsets) with an architecture that may vary depending on manufacturer (for example, INTEL, AMD, ARM, etc.). INTEL is a registered trademark of Intel Corporation in the United States and other countries. AMD is a registered trademark of Advanced Micro Devices, Inc. in the United States and other countries. ARM is an unregistered trademark of ARM Holdings plc in the United States and other countries. The architecture of the chipset 210 includes a core and memory control group 220 and an I/O controller hub 250 that exchanges information (for example, data, signals, commands, etc.) via a direct management interface (DMI) 242 or a link controller 244. In FIG. 2, the DMI 242 is a chip-to-chip interface (sometimes referred to as being a link between a "northbridge" and a "southbridge"). The core and memory control group 220 include one or more processors 222 (for example, single or multi-core) and a memory controller hub 226 that exchange information via a front side bus (FSB) 224; noting that components of the group 220 may be integrated in a chip that supplants the conventional "northbridge" style architecture. One or more processors 222 comprise internal arithmetic units, registers, cache memory, busses, I/O ports, etc., as is well known in the art.

In FIG. 2, the memory controller hub 226 interfaces with memory 240 (for example, to provide support for a type of RAM that may be referred to as "system memory" or "memory"). The memory controller hub 226 further includes a low voltage differential signaling (LVDS) interface 232 for a display device 292 (for example, a CRT, a flat panel, touch screen, etc.). A block 238 includes some technologies that may be supported via the LVDS interface 232 (for example, serial digital video, HDMI/DVI, display port). The memory controller hub 226 also includes a PCI-express interface (PCI-E) 234 that may support discrete graphics 236.

In FIG. 2, the I/O hub controller 250 includes a SATA interface 251 (for example, for HDDs, SDDs, etc., 280), a PCI-E interface 252 (for example, for wireless connections 282), a USB interface 253 (for example, for devices 284 such as a digitizer, keyboard, mice, cameras, phones, microphones, storage, other connected devices, etc.), a network interface 254 (for example, LAN), a GPIO interface 255, a LPC interface 270 (for ASICs 271, a TPM 272, a super I/O 273, a firmware hub 274, BIOS support 275 as well as various types of memory 276 such as ROM 277, Flash 278, and NVRAM 279), a power management interface 261, a clock generator interface 262, an audio interface 263 (for example, for speakers 294), a TCO interface 264, a system management bus interface 265, and SPI Flash 266, which can include BIOS 268 and boot code 290. The I/O hub controller 250 may include gigabit Ethernet support.

The system, upon power on, may be configured to execute boot code 290 for the BIOS 268, as stored within the SPI Flash 266, and thereafter processes data under the control of one or more operating systems and application software (for example, stored in system memory 240). An operating system may be stored in any of a variety of locations and accessed, for example, according to instructions of the BIOS 268. As described herein, a device may include fewer or more features than shown in the system of FIG. 2.

Information handling device circuitry, as for example outlined in FIG. 1 or FIG. 2, may be used in devices such as tablets, smart phones, personal computer devices generally, and/or electronic devices which users may use in or with systems as described herein. For example, the circuitry outlined in FIG. 1 may be implemented in a tablet or smart phone embodiment, whereas the circuitry outlined in FIG. 2 may be implemented in a personal computer embodiment.

Figure 3:
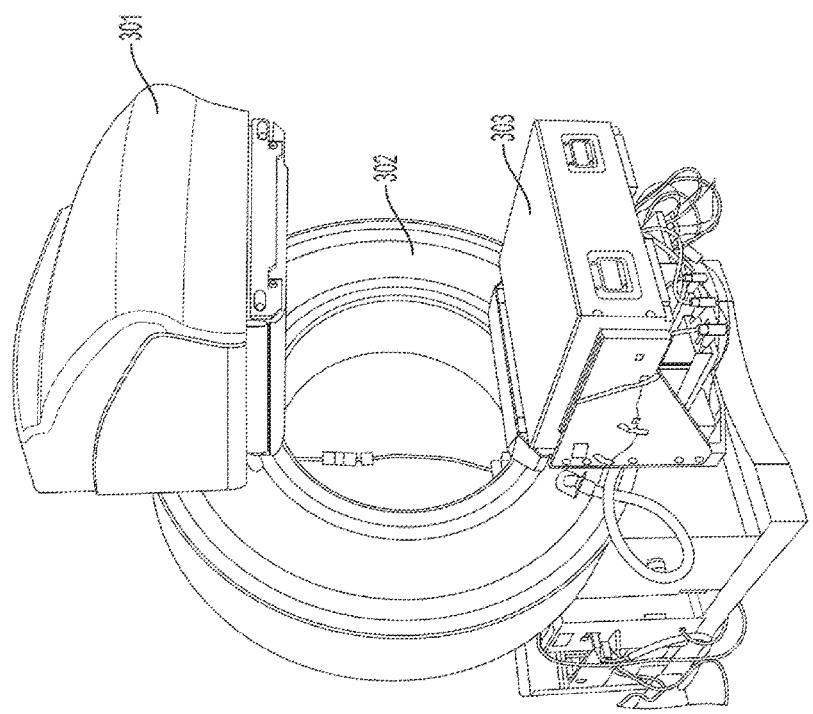
FIG. 3 illustrates an embodiment of an imaging device that may use the disclosed embodiments.

Referring now to FIG. 3, an illustrative embodiment of an imaging system is shown. An embodiment has a bed for a patient to be imaged and the bed may be moveable and placed in a gantry 302. The gantry may have an opening such that the patient may be inserted into the gantry. The positioning of the patient within the gantry may place the area of interest of the patient's body between an emission source and a receiving device. In another embodiment, the patient may be injected with the emission source prior to or during the imaging procedure, in which case there may be two or more receiving devices 301 and 302. The gantry may be movable or rotatable. For example, the gantry and associated emission and receiving equipment may be rotated 360 degrees around a patient. Other movement of the gantry is contemplated. The gantry movement may be a smooth motion, step-wise, repetitive, or the gantry may be in a static position depending on the imaging needs of the procedure. Healthcare imaging is an illustrative embodiment, other embodiments are disclosed.

In an embodiment, the imaging device may be installed in a location for security scanning. For example, the device may be in an airport security checkpoint, a baggage screening location, or the like. In an embodiment, the imaging device may be permanently anchored, moveable, or completely portable. For example, an imaging device may be a hand-held device for use by first responders, security, or assessment teams. Other uses outside of a security setting are contemplated and are disclosed. As should be understood by one skilled in the art, both healthcare imaging and security screening are merely examples. Other possible applications for the techniques as described herein are possible and contemplated.

In an embodiment, the receiving equipment may contain sensors that are sensitive to radiological particles or photons. The receiving equipment may record communication events on an array of sensors located in the receiving equipment. Each of the sensors in the array may be represented as a pixel in the final image. During the course of imaging, malfunctions may occur, resulting in non-conforming pixels that may not capture and send proper communication events to be used in creating an image or for analysis. In an embodiment, one or more non-conforming pixels may be masked to prevent the use of information from the one or more non-conforming pixels. An embodiment masks the one or more non-conforming pixels to allow imaging without erroneous data. In a healthcare setting this may allow healthcare professionals to achieve better imaging without interruption to the procedure which may result in better treatment plans and decrease medical costs. For example, rather than requiring a service technician to physically access the device and manually mask the non-conforming pixels, the system as described herein automatically takes steps to recognize a non-conforming pixel and mask the pixel without human intervention.

Figure 4:
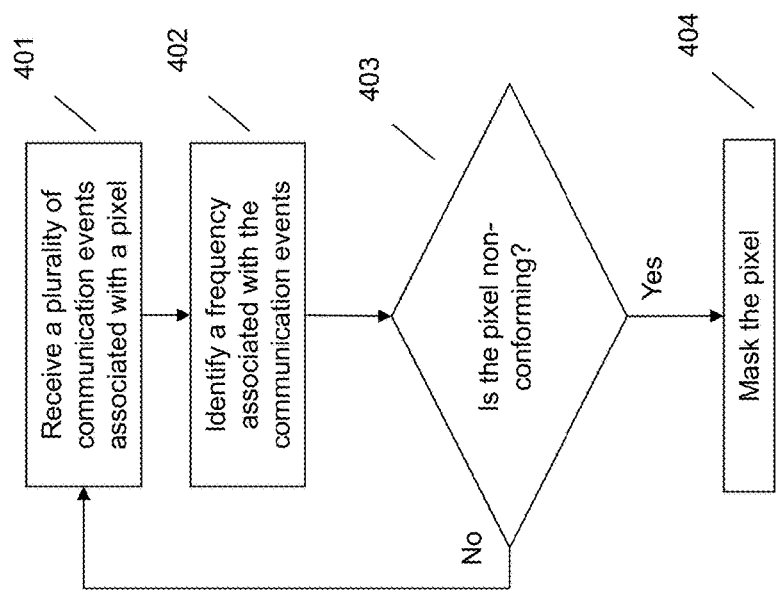
FIG. 4 illustrates a method of non-conforming pixel masking.

FIG. 4 illustrates a technique for automatically identifying a non-conforming pixel and masking the non-conforming pixel. In an embodiment an imaging device may receive a plurality of communication events associated with a pixel of an imaging device at 401. As mentioned above, an embodiment of an imaging device may be in a healthcare setting, security screening, manufacturing, or any application where an imaging device may be utilized. For example, the imaging device may be a radiological imaging device in which radiological matter (consisting of particles or photons) is either transmitted through or injected into a patient's body. Another example may include an airport or port of entry device used to scan for radiation or other material of interest for security purposes. Another example of an imaging device may be used by first responder to determine environmental conditions and/or safety of a location. Other uses are contemplated and disclosed.

In an embodiment a pixel (picture element) refers to a discrete location on the imaging hardware surface that may be only a subset of the imaged area. The data or communication from a pixel or plurality of pixels may be used to form an image as a composite from the one or more pixels. An imaging device may use many methods to detect a communication event from a pixel. For example, in a consumer camera a pixel represents the wavelength of the visible light detected by the pixel. As another example, radiological imaging devices, for example, those used in cancer screenings, radiation detectors, and the like, use a type of atomic particle or photon emitted by a source and measurable by a sensor with associated circuitry to provide both a location and intensity (or count density) of the radiological particles or photons detected. Using the communication events from the pixels, an image may be created based upon the location, intensity, and energy or wavelength of the communication event from the pixel. In other words, an embodiment may use the signal transmitted from the pixel during imaging to create an image based upon the information contained within the signal. The data may be collected from multiple pixels to create an image of a larger area.

In an embodiment, the method and system may identify a frequency associated with communication events at 402. Identification of a frequency may comprise making a determination or identification of a number of communication events within a predetermined time interval. For example, an embodiment may determine how many communications events have been received from a pixel within a preset time interval (e.g., 5 seconds, half a millisecond, ten milliseconds, etc.). In an embodiment, the identification of a frequency may alternatively include determining a time interval between sequential communication events or an average time interval between communication events. As an example, an embodiment may determine how long has it been since the pixel last provided a communication event. In other words, determining a frequency may include identifying how many communication events have been received in a time interval or how closely spaced the communications events occur. A pixel providing many communication events closely spaced together may be indicative of a hot or overactive pixel.

In other words, an embodiment may use an algorithm for determination of a non-conforming pixel and identification of the non-conforming pixel may be based on at least two parameters, for example, an upper and a lower threshold frequency. If a pixel sends a certain number of communication events in a period of time, whether too many (more than the upper threshold) or too few (less than the lower threshold), the pixel may be determined to be non-conforming. Alternatively, the communication event frequency may be measured by the time interval between triggers for the same channel. Communication events that are too frequent (shorter time interval than the lower threshold) or not frequent enough (longer time interval than the upper threshold) as determined by the disclosed thresholds may label the pixel as non-conforming. In other words, when a pixel sends a communication the event is logged and tracked, for example, on a temporal scale. The system may then use the logged communication events to determine how many communication events have been received and how often the communication events were received from a particular pixel.

For illustration, if the pixels were likened to participants in a meeting, one measure of frequency may track how many times a given participant talks during the meeting, and the alternative measure may track how long it has been since that participant spoke last in the meeting.

Based upon the frequency associated with the communication events, the system may determine whether the pixel is a non-conforming pixel at 403. Identifying a pixel as a non-conforming pixel may include identifying that the frequency of communication events is greater than a predetermined threshold. In an embodiment a user, healthcare provider, first responder, security team member, technician, programmer, or the like, may set a predetermined threshold for a frequency of communication events. For example, a user or the like may set a threshold as 1000 events in a 1 minute time period. The threshold may also be adjusted "on the fly" during an imaging session to obtain a better final image or data. The threshold may also be determined by the system during operation or may be dynamically adjusted during operation. If a pixel reaches a frequency of communication events above that selected threshold, the system may turn off, ignore, or mask that pixel. In an embodiment, a threshold may also be set as a lower limit. For example, a pixel may be masked if the frequency falls below a set threshold, which may be indicative of a dead pixel. In an embodiment, both an upper and lower limit may be selected creating the possibility to mask pixels either in a certain range or above and below set thresholds. In an embodiment, a threshold may be determined locally by comparing the frequency of communication events from a pixel to its neighbors.

In an embodiment, determining whether a pixel comprises a non-conforming pixel may be determined using a score associated with the pixel. For example, each pixel may have an associated score that can be adjusted periodically based upon communication events received from the pixel. If the communication events from the pixel fall outside the predetermined threshold, the score may be increased. For example, updating the score may include increasing the score if the number of communication events is greater than a predetermined threshold number of communication events within the predetermined time interval. If the communication events from the pixel fall within the predetermined threshold, the score may be decreased but not to a value less than zero. For example, updating a score includes decreasing the score if the number of communication events is less than a predetermined number of communication events within the predetermined time interval.

As communication events are received from the pixel the score may be dynamically adjusted based upon the adherence of the communication events to the threshold, range, or other comparison value. The system may then identify the pixel as a non-conforming pixel when the score associated with the pixel reaches or exceeds a predetermined threshold. Alternatively, the pixel may be identified as a non-conforming pixel if the score associated with the pixel is significantly different when compared with neighboring pixels, for example, if the score of the pixel is much greater than the score associated with neighboring pixels. The use of this type of scoring model provides a technique for ensuring that pixels that are masked are actually non-conforming pixels. In other words, during normal operation, a pixel may sometimes provide communication events that are outside the frequency threshold even if the pixel is working normally according to radiation statistics (Poisson). Accordingly, the use of the scoring technique provides for allowance of these normal statistical events.

In an embodiment, the algorithm may use other data to determine if a pixel is non-conforming. For example, one embodiment may use not just a frequency of event communications, but may also use an intensity of a communication event as a criteria for a determining non-conformity. Other system parameters, such as thermal data, bandwidth, connectivity, or the like may also be used for determining whether a pixel may be non-conforming. For example, if pixel-associated elements overheat and begin to operate outside of a thermal threshold, then the pixel may be non-conforming. As another example, if a pixel uses much more bandwidth for event communication, then the pixel may be determined to be non-conforming. The system and method contemplates that any data collected by the imaging device to be useful in the determination of a non-conforming pixel.

If the system determines that the pixel is not a non-conforming pixel (thus the pixel is conforming) at 403, the system may continue to receive communication events from the pixel at 401. In other words, if the system determines a pixel is within a threshold, then the system may continue to receive information from the pixel in the course of the imaging procedure. A conforming pixel may continue to provide communication events to a stream of data along with other conforming pixels to produce an image.

If, however, the pixel is determined to be a non-conforming pixel at 403, the system may mask the pixel at 404. Masking the pixel may include using one or more of a variety of techniques to prevent communication from the pixel. For example, one technique for masking the pixel may include turning off or ignoring communication events received from the pixel communication channel. As another example, one technique for masking the pixel may include turning off the pixel so that it does not provide any communication events at all. Still another technique may include disregarding any communication events received from the pixel. In other words, the communication events may be received but thereafter disregarded or discarded for use producing an image.

In an embodiment, a pixel may be masked for different time periods or even permanently. For example, if a pixel is identified as non-conforming pixel, the system may mask the non-conforming pixel very briefly, for example, for the duration of the imaging session, until a power cycle of the system, until a reset event, until a technician or user unmasks the pixel, or the like. The pixel may also be masked permanently. In other words, the pixel may be masked and remain masked even in the event of a power cycle, system reset, or the like. The only way to unmask a permanently masked pixel may be by a technician or other user manually reinstating the pixel.

Data collected with respect to non-conforming pixels may be tracked in real-time both on and offsite, or saved to a log for later analysis by the system, user, technician, or manufacturer. For example, in an embodiment, a non-conforming pixel may be added to a list including non-conforming pixels. The list may be in a format to allow the system or a user to determine when a pixel became non-conforming, how often a pixel becomes non-conforming, how far out of range from a threshold the pixel was during imaging, how the non-conforming pixels neighbors within the array were performing, and the like. List data may be useful to track the history and real-time performance of a non-conforming pixel and performance of other pixels in an array. For example, if a particular pixel frequently is determined to be non-conforming, for example after a reset, the pixel may be indicated as a troublesome pixel. A pixel that is non-conforming frequently may be identified for diagnostics, calibration, replacement, or the like.

Additionally, the list or other tracking mechanism may be used to determine when a pixel should be permanently masked. For example, if a pixel continues to get added to the list, the system may determine that the pixel is troublesome and may permanently mask the pixel. The determination that the pixel should be permanently masked may be dependent on a threshold value for list addition. For example, if the pixel is added to the list more than three times, the system may determine that the pixel should be permanently masked. As another example, if the pixel is added to the list a predetermined number of times within a predetermined time period (e.g., three times in the last two months, four times in the last five imaging operations, 70% of the time, etc.) the system may determine that the pixel should be permanently masked. The value, threshold, or frequency for determination of permanent masking may be a default value, set by a user, or dynamically adjusted. Alternatively, rather than the system automatically determining whether a pixel should be permanently masked, a technician or other user may make that determination.

In an embodiment, the process of determining if a pixel is non-conforming is an ongoing process that can occur during imaging and may be based upon historical information regarding the pixel and pixel communication events. The determination of whether a pixel is non-conforming may occur at a set time or may occur on a continuous basis. For example, the system may detect non-conforming pixels continuously, periodically, at the beginning of imaging, the end of a procedure, or any combination thereof or other times. In an embodiment, the time for detection of a non-conforming pixel may be set by a user, a default value, or the like. Additionally, masking of a non-conforming pixel may occur at set times or whenever the pixel is identified as non-conforming. In an embodiment the masking may occur within the imaging device itself. Additionally or alternatively, the masking may occur at a remote site such as a device receiving the data communication events from the imaging device, a remote location, a cloud server, operational command, or the like.

In an embodiment, data associated with the non-conforming pixels may be replaced with image data. This replacement image data may be based upon other pixels. In other words, if a pixel is determined to be non-conforming and no further communication events are received from the non-conforming pixel, a "hole" or black area on the image may be observed. To rectify this "hole" in the image, an image correction technique may be employed. One common image correction technique uses data from neighboring pixels, or other pixels in proximity to the non-conforming pixel. It should be understood that a neighbor pixel does not have to be directly adjacent to a non-conforming pixel. Rather, neighboring pixels may include pixels within a particular range or proximity to the non-conforming pixel.

In an embodiment, non-conforming pixel data may be inferred, interpolated, or the like, using the neighboring pixel data. In one image correction technique, the non-conforming data may be "filled in" by conforming neighboring pixels. For example, if a non-conforming pixel has conforming neighbors and the neighbor communication events are all similar, the data from a neighboring pixel may be used for the non-conforming pixels. In another example, if the non-conforming pixel has conforming pixel neighbors that show a gradient across a space, the non-conforming pixel may be assigned a value within that gradient that matches the neighboring gradient pattern. In an embodiment, different mathematical methods may be used to infer non-conforming event data such as averaging, median, spline, interpolation, weighted averaging, event histograms, rasters, detection of communication event in patterns across the array, or the like.

In some applications, the non-conforming pixel's own data from a time before becoming non-conforming may be used to extrapolate replacement pixel data. In an embodiment, the imaging device may be physically shifted such that conforming pixels may then image areas previously associated with a non-conforming pixel. For example, a gantry and associated imaging device may be rotated about a patient body. In some procedures the target to be imaged may be moving, such as a bolus of radioactive agent travelling through a vasculature. If the target is moving, the method may make a prediction of where an imaging target may be and at what intensity as the target moves across the array from a conforming to a non-conforming to a conforming pixel. The non-conforming pixel communication events may be inferred from the neighbors which may capture data before and after the movement across a non-conforming pixel.

Figure 5:
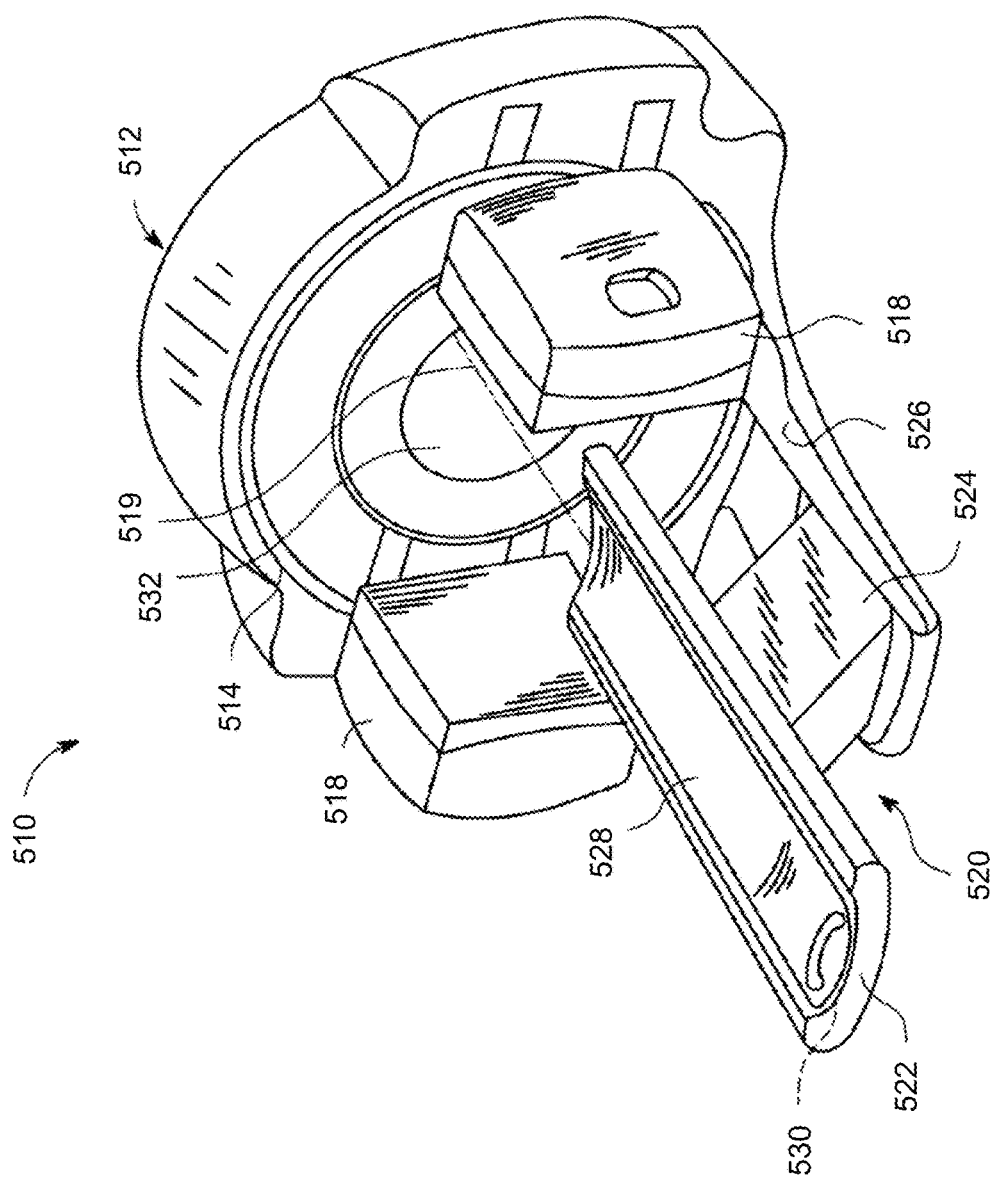
FIG. 5 illustrates another embodiment of an imaging device that may use the disclosed embodiments.

Referring now to FIG. 5, the pixelated detectors of the various embodiments may be provided as part of different types of imaging systems, for example, nuclear medicine (NM) imaging systems such as positron emission tomography (PET) imaging systems, single-photon emission computed tomography (SPECT) imaging systems and/or x-ray imaging systems and x-ray computed tomography (CT) imaging systems, among others. For example, FIG. 5 is a perspective view of an exemplary embodiment of a medical imaging system 510 constructed in accordance with various embodiments, which in this embodiment is a SPECT imaging system similar to FIG. 3. The system 510 includes an integrated gantry 512 that further includes a rotor 514 oriented about a gantry central bore 532. The rotor 514 is configured to support one or more NM pixelated cameras 518 (two cameras 518 are shown), such as, but not limited to gamma cameras, SPECT detectors, multi-layer pixelated cameras (e.g., Compton camera) and/or PET detectors. It should be noted that when the medical imaging system 510 includes a CT camera or an x-ray camera, the medical imaging system 510 also includes an x-ray tube (not shown) for emitting x-ray radiation towards the detectors. In various embodiments, the cameras 518 are formed from pixelated detectors as described in more detail herein. The rotors 514 are further configured to rotate axially about an examination axis 519.

A patient table 520 may include a bed 522 slidingly coupled to a bed support system 524, which may be coupled directly to a floor or may be coupled to the gantry 512 through a base 526 coupled to the gantry 512. The bed 522 may include a stretcher 528 slidingly coupled to an upper surface 530 of the bed 522. The patient table 520 is configured to facilitate ingress and egress of a patient (not shown) into an examination position that is substantially aligned with examination axis 519. During an imaging scan, the patient table 520 may be controlled to move the bed 522 and/or stretcher 528 axially into and out of a bore 532. The operation and control of the imaging system 510 may be performed in any manner known in the art. It should be noted that the various embodiments may be implemented in connection with imaging systems that include rotating gantries or stationary gantries.

Figure 6:
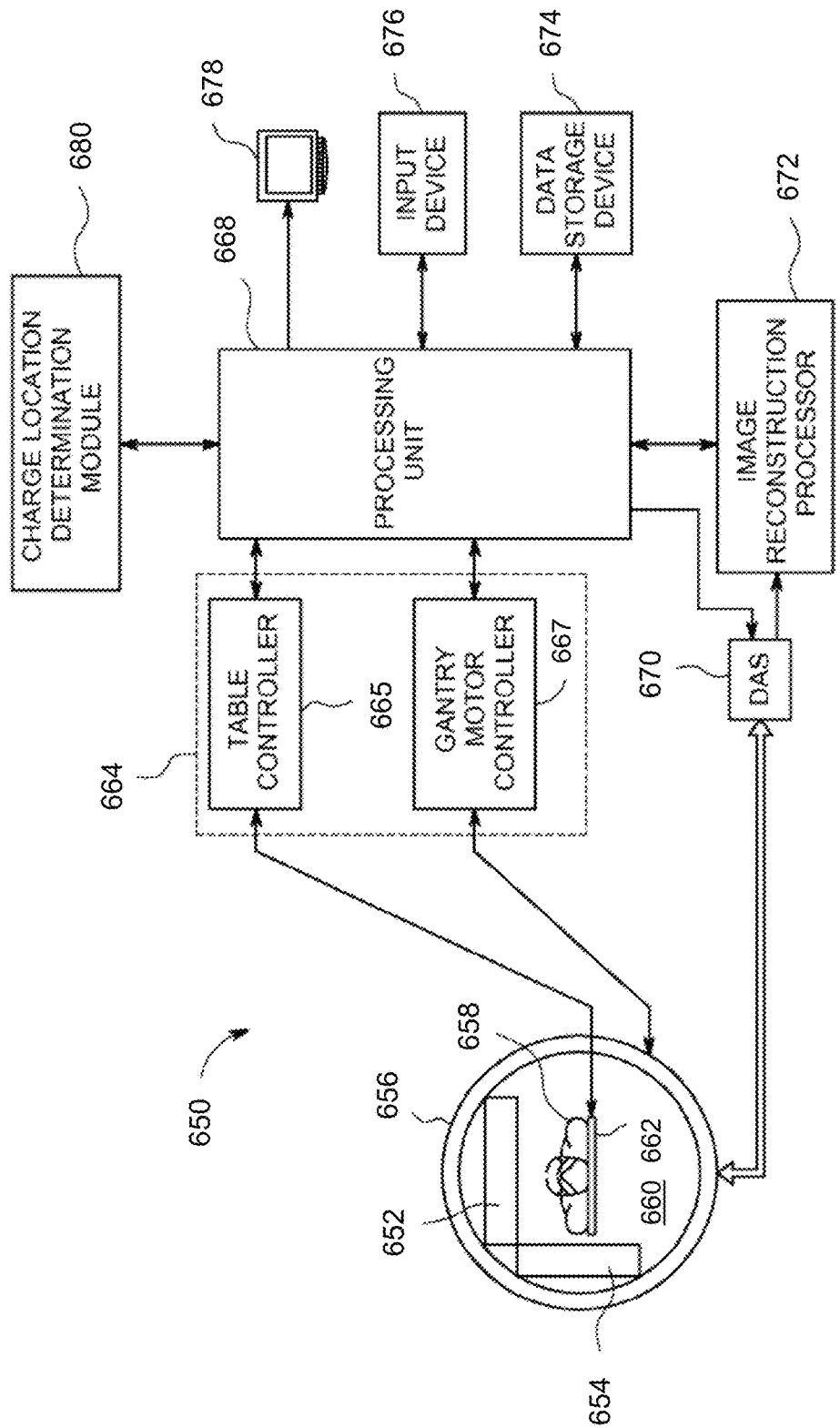
FIG. 6 illustrates a further example of information handling device circuitry.

Referring now to FIG. 6, which illustrates a block diagram illustrating an imaging system 650 that has a plurality of pixelated imaging detectors configured in accordance with various embodiments mounted on a gantry. It should be noted that the imaging system may also be a multi-modality imaging system, such as an NM/CT imaging system. The imaging system 650, illustrated as a SPECT imaging system, generally includes a plurality of pixelated imaging detectors 652 and 654 (two are illustrated) mounted on a gantry 656. It should be noted that additional imaging detectors may be provided. The imaging detectors 652 and 654 are located at multiple positions (e.g., in an L-mode configuration, as shown) with respect to a patient 658 in a bore 660 of the gantry 656. The patient 658 is supported on a patient table 662 such that radiation or imaging data specific to a structure of interest (e.g., the heart) within the patient 658 may be acquired. It should be noted that although the imaging detectors 652 and 654 are configured for movable operation (azimuthally around, radially in or out, rotatably around an axis, tiltably about a pivot, and the like) of the gantry 656, in some imaging systems, imaging detectors are fixedly coupled to the gantry 656 and in a stationary position, for example, in a PET imaging system (e.g., a ring of imaging detectors). It also should be noted that the imaging detectors 652 and 654 may be formed from different materials as described herein and provided in different configurations known in the art, such as flat or curved panels.

One or more collimators may be provided in front of the radiation detection face (not shown) of one or more of the imaging detectors 652 and 654. The imaging detectors 652 and 654 acquire a 2D image that may be defined by the x and y location of a pixel and the location of the imaging detectors 652 and 654. The radiation detection face (not shown) is directed towards, for example, the patient 658, which may be a human patient, animal, airport baggage, or the like.

A controller unit 664 may control the movement and positioning of the patient table 662 with respect to the imaging detectors 652 and 654 and the movement and positioning of the imaging detectors 652 and 654 with respect to the patient 658 to position the desired anatomy of the patient 658 within the fields of view (FOVs) of the imaging detectors 652 and 654, which may be performed prior to acquiring an image of the anatomy of interest. The controller unit 664 may have a table controller 665 and a gantry motor controller 667 that each may be automatically commanded by a processing unit 668, manually controlled by an operator, or a combination thereof. The table controller 665 may move the patient table 662 to position the patient 658 relative to the FOV of the imaging detectors 652 and 654. Additionally, or optionally, the imaging detectors 652 and 654 may be moved, positioned or oriented relative to the patient 658 or rotated about the patient 658 under the control of the gantry motor controller 667.

The imaging data may be combined and reconstructed into an image, which may comprise 2D images, a 3D volume or a 3D volume over time (4D).

A Data Acquisition System (DAS) 670 receives analog and/or digital electrical signal data produced by the imaging detectors 652 and 654 and decodes the data for subsequent processing as described in more detail herein. An image reconstruction processor 672 receives the data from the DAS 670 and reconstructs an image using any reconstruction process known in the art. A data storage device 674 may be provided to store data from the DAS 670 or reconstructed image data. An input device 676 also may be provided to receive user inputs and a display 678 may be provided to display reconstructed images. A charge location determination module 680 may provide x and y position for each gamma photon interaction the pixelated imaging detectors 652 and 654. In an embodiment, a depth-of-interaction z position may be determined.

The various embodiments described herein thus represent a technical improvement to imaging devices that may require high sensitivity to the material imaged. An embodiment allows for the automatic detection and masking of one or more pixels determined to be non-conforming. Using the techniques described herein, rather than requiring a technician or other user to manually mask the non-conforming pixel, the system can automatically identify and mask the non-conforming pixel. This results in more accurate imaging, less device down-time, and lower costs associated with the imaging procedure.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, comprising:
receiving a plurality of communication events associated with a pixel of an imaging device;
identifying a frequency associated with the communication events, wherein the identifying a frequency comprises determining a number of communication events occurring within a predetermined time interval or determining a time interval between the communication events;
resolving, from the identified frequency, whether the pixel comprises a non-conforming pixel by updating a score associated with the pixel, wherein the updating a score comprises increasing the score if the number of communication events is greater than a predetermined number of communication events within the predetermined time interval and wherein the updating a score comprises decreasing the score if the number of communication events is less than a predetermined number of communication events within the predetermined time interval; and
masking, if the pixel comprises a non-conforming pixel, subsequent communication events from the non-conforming pixel.

2. The method of claim 1, wherein the determining a number of communication events comprises determining that the number of communication events occurring within a predetermined time interval is greater than a predetermined number of communications events or that the time interval between communication events is less than a threshold time interval.

3. The method of claim 1, wherein the resolving further comprises identifying the pixel as non-conforming when the score reaches a predetermined threshold.

4. The method of claim 1, wherein the masking comprises disregarding communication events associated with the pixel.

5. The method of claim 1, further comprising adding the non-conforming pixel to a non-conforming pixel list comprising non-conforming pixels.

6. The method of claim 5, further comprising determining a number of times the non-conforming pixel has been added to the non-conforming pixel list.

7. The method of claim 6, further comprising, responsive to determining that the number of times the non-conforming pixel has been added to the non-conforming pixel list is greater than a predetermined threshold, permanently masking the non-conforming pixel.

8. The method of claim 1, further comprising replacing image data associated with the non-conforming pixel within image data based upon data from a plurality of pixels neighboring the non-conforming pixel.

9. An information handling device, comprising:
a processor;
a memory device that stores instructions executable by the processor to:
receive a plurality of communication events associated with a pixel of an imaging device;

identify a frequency associated with the communication events, wherein the identifying a frequency comprises determining a number of communication events occurring within a predetermined time interval or determining a time interval between the communication events;

resolve, from the identified frequency, whether the pixel comprises a non-conforming pixel by updating a score associated with the pixel, wherein the updating a score comprises increasing the score if the number of communication events is greater than a predetermined number of communication events within the predetermined time interval and wherein the updating a score comprises decreasing the score if the number of communication events is less than a predetermined number of communication events within the predetermined time interval; and mask, if the pixel comprises a non-conforming pixel, subsequent communication events from the non-conforming pixel.

10. The information handling device of claim 9, wherein to determine a number of communication events comprises determining that the number of communication events occurring within a predetermined time interval is greater than a predetermined number of communications events or that the time interval between communication events is less than a threshold time interval.

11. The information handling device of claim 9, wherein to resolve further comprises identifying the pixel as non-conforming when the score reaches a predetermined threshold.

12. The information handling device of claim 9, wherein to mask comprises disregarding communication events associated with the pixel.

13. The information handling device of claim 9, further comprising adding the non-conforming pixel to a non-conforming pixel list comprising non-conforming pixels.

14. The information handling device of claim 13, further comprising determining a number of times the non-conforming pixel has been added to the non-conforming pixel list.

15. The information handling device of claim 14, further comprising, responsive to determining that the number of times the non-conforming pixel has been added to the non-conforming pixel list is greater than a predetermined threshold, permanently masking the non-conforming pixel.

16. The information handling device of claim 9, further comprising replacing image data associated with the non-conforming pixel within image data based upon data from a plurality of pixels neighboring the non-conforming pixel.

17. A product, comprising:
a storage device that stores code, the code being executable by a processor and comprising:
code that receives a plurality of communication events associated with a pixel of an imaging device;
code that identifies a frequency associated with the communication events, wherein the identifying a frequency comprises determining a number of communication events occurring within a predetermined time interval or determining a time interval between the communication events;
code that resolves, from the identified frequency, whether the pixel comprises a non-conforming pixel by updating a score associated with the pixel, wherein the updating a score comprises increasing the score if the number of communication events is greater than a predetermined number of communication events within the predetermined time interval and wherein the updating a score comprises decreasing the score if the number of communication events is less than a predetermined number of communication events within the predetermined time interval; and
code that masks, if the pixel comprises a non-conforming pixel, subsequent communication events from the non-conforming pixel.

* * * * *